United States Patent [19]
Björklund

[11] 4,160,018
[45] Jul. 3, 1979

[54] STABILIZED CANCER ASSOCIATED POLYPEPTIDE ANTIGEN AND PREPARATION THEREOF

[76] Inventor: Knut B. Björklund, Appelviksvägen 26,, 161 36 Bromma, Sweden

[21] Appl. No.: 664,258

[22] Filed: Mar. 5, 1976

Related U.S. Application Data

[60] Division of Ser. No. 373,004, Jun. 25, 1973, Pat. No. 3,960,827, which is a continuation-in-part of Ser. No. 270,273, Jul. 10, 1972, abandoned.

[51] Int. Cl.² .................. A61K 37/00; A61K 39/00; C07G 7/00; G01N 31/00
[52] U.S. Cl. .................. 424/12; 260/112 R; 260/112 B; 260/112.5; 260/121; 424/8; 424/85; 424/88; 424/95; 424/177
[58] Field of Search .................. 424/8, 12, 85, 88, 95, 424/177; 260/112 R, 112 B, 112.5, 121

[56] References Cited

U.S. PATENT DOCUMENTS

| | | | |
|---|---|---|---|
| 3,010,875 | 11/1961 | Cappel | 424/13 |
| 3,551,555 | 12/1970 | Schuurs | 424/12 |
| 3,823,126 | 7/1974 | Bjorklund | 424/88 X |
| 3,968,827 | 6/1976 | Bjorklund | 260/112 R |

OTHER PUBLICATIONS

Björklund, Immuno. Techniq. for Detection of Cancer, Bonniers, Stockholm, Sweden, 1973, pp. 193–194, 237–247.
Björklund, Int. Arch. Allergy, vol. 8, 1956, pp. 179–192.
Björklund, Int. Arch. Allergy, vol. 36, 1969, pp. 191–203.
Björklund, reprint from Protides of the Biological Fluids, 24th Colloquium, Bruges 1975, Pergamon Press, Oxford 1976.
Björklund, reprint from J. Nat. Cancer Inst., vol. 26, Mar. 1961, pp. 533–545.
Björklund, reprint from Analytical Biochem., vol. 41, No. 1, May 1971, pp. 287–290.
Björklund, reprint from The Relic. Sys. in Health & Dis.: Immuno & Path. Aspects (1976), Plenum Pub., N.Y., pp. 357–370.
Björklund, reprint from Onco-Developmental Gene Expression, Acd Press, N.Y., 1976, pp. 501–508.

*Primary Examiner*—Anna P. Fagelson
*Attorney, Agent, or Firm*—Gordon W. Hueschen

[57] ABSTRACT

A process for the isolation of cancer associated polypeptide antigen mainly by several steps of gel filtration and pH-gradient elution; a cancer associated polypeptide antigen based on a single peptide chain and denaturating irreversibly at pHs exceeding about 4.5; a composition comprising such antigen and a stabilizing amount of albumen in admixture therewith and a method of making such composition; a diagnostic composition comprising a particulate material labelled with albumen-stabilized antigen; process for preparing antibodies monospecific with regard to the cancer associated polypeptide antigen comprising preparing an oil emulsion, wherein an acid aqueous solution of the polypeptide is enclosed phase protected by a surrounding oil phase; a cancer diagnosis method based on determining the presence of cancer associated polypeptide antigen in a living animal body under examination; and composition useful as an immunizing agent containing as an active ingredient the cancer associated polypeptide antigen.

6 Claims, No Drawings

STABILIZED CANCER ASSOCIATED POLYPEPTIDE ANTIGEN AND PREPARATION THEREOF

The present application is a division of my prior-filled co-pending application, Ser. No. 373,004, filed June 25, 1973, now U.S. Pat. No. 3,960,827, issued June 1, 1976, which in turn is a continuation-in-part of my prior-filled co-pending application Ser. No. 270,273, filed July 10, 1972 now abandoned.

The present invention refers to the problem of isolating cancer associated antigen showing monospecificity and being present in a wide variety of human cancers of different localizations.

Many attempts have been made to demonstrate the presence of tumor-reactive antibodies in sera obtained from animals to which preparations of human cancer tumors have been administered. If such demonstrations would turn out to be consistently reproducible, that would indicate the presence in human cancer tissue of important antigens not present in the normal tissues and might thus lead to a better understanding of the nature of the neoplastic process. For the purpose of a better understanding of cancer diseases, human cancer tissue has been studied in order to find out the existence of monospecific cancer associated antigen and above all to find out a reproducible way of isolating and purifying such antigen.

The presence of antigens associated with adenocarcinoma of the colon and the digestive system has been shown by Gold et al.; J. expt. Med. 121 (1965) 439–462 and J.expt. Med. 122, 1965 467–487. In these reports reference is had to even earlier works by B. Björkland indicating the existence of human cancer associated antigen common to the major part of all known malignant tumors of epithelial origin, Internat. Arch. Allergy and Appl. Immunol. 1966, 8, 179 and Internat. Arch. Allergy and Appl. Immunol. 1958, 12, 241. In U.S. Pat. No. 3,663,684 to Freedman et al. there is described a carcinomembryonic antigen showing so called "CEA-activity". This antigen is, however, completely different from the antigen of this invention, which will be shown in detail below in this disclosure.

A practical and commercially useful isolation of antigen per se as well as its association with various carcinomatous diseases has not hitherto been achieved. Thus, it has hitherto not been possible to isolate and characterize human cancer associated antigen by practical and reproducible methods, neither has it been possible to establish or even to indicate the presence of the antigen in the blood of persons suffering from hidden or overt cancerous disease by means of a diagnostic test suitable for the investigation in a large scale.

For the purpose of fully utilizing the presence of antibodies specific to tumor associated antigen in animal antisera as a diagnostic agent a test must be developed which shows the existence of the tumor antigen in the blood of the patient. Procedures suggested up to now have not proved to be effective when trying to make a certain diagnosis with regard to the presence of cancer disease.

One of the main objects of the invention is to provide a process for isolating and purifying cancer associated antigen starting from human tumor tissue or other tissue containing such antigen.

Another object of the invention is to characterize such antigen after its isolation.

A further object of the invention is to provide diagnostic test procedure based on the use or existence of such human cancer associated antigen.

A further object of the invention is to provide a process for preparing antibodies specific to said cancer associated polypeptide antigen.

Still a further object of the invention is to provide a composition useful as an immunizing agent.

Yet another object of the invention is to provide a composition comprising such antigen and a stabilizing amount of albumen in admixture therewith and a method of making such composition.

A further object of the invention is to provide a diagnostic composition comprising a particulate material labelled with albumen-stabilized antigen.

In this disclosure including the claims the expression "cancer associated polypeptide antigen" is abbreviated CAPA.

Accordingly, the invention provides i.a. practical processes for:

(a) Purifying, isolating, characterizing and confirming the identity and specificity of CAPA;

(b) Use of such CAPA for diagnosing the presence of cancer by indicating the presence of circulating CAPA; and (c) A process for the preparation of antibodies monospecific to such CAPA.

Other objects and characterizing features of the invention will be obvious from the following description of the invention in general terms as well as by specific examples.

A material possessing CAPA activity is isolated and purified by means of the process of the present invention by homogenizing malignant tissues from autopsies, carcinoma tissues of various types and sites being collected to make up a tumor pool. An alternative starting material is tissue from human placenta or cultures of malignant cells in vitro (for details on such cultures see B. Björklund, V. Björklund and I. Hedlöf, J.Nat. Cancer Inst. 26: 533–545, 1961, "Antigenicity of Pooled Human Malignant and Normal Tissues by Cytoimmunological Technique. III. Distribution of Tumor Antigen." Normal tissues are also collected in parallel with malignant tissues, and to arrive at a useful sequence of process steps leading to the isolation of a pure antigen a new test procedure has been developed as per the enclosed Chart. Thus, the application of biochemical separation methods was guided by a sensitive immunological assay procedure permitting the detection of less than 1 ng (nanograms) of antigen. The greatest value of the assay technique as per Chart is based on its selectively. Antigenic differences between extracts to be compared were manifested against a background of insignificant similarities, the assay arrangement serving as a feedback control of an array of chemical procedures which were varied to result in tumor fractions of (1) maximum antigenic reactivity with anti-tumor sera which had been absorbed by normal antigens; and of (2) minimum antigenic reactivity with anti-tumor sera which has been absorbed by tumor antigens. For additional control purposes there were also established tumor fractions of minimum reactivity with anti-normal sera which had been absorbed by normal or tumor antigens.

Carcinoma and normal tissues while in the frozen state are separately mixed with water having a temperature of about 0° C. and are homogenized in such a way as not to generate excess friction heat which will cause inactivation of the pertinent CAPA. The temperature of the suspension should not be allowed to rise above about 0° C.

The resulting cold mixture of liquid homogenate and solids is mixed with an organic solvent having the ability of dissolving lipids, such as neutral fats, for instance acetone or ethyl ether, at a temperature below about 0° C., the solvent treatment having for its purpose the removal of i.a. lipoidic substances and resulting in increased exposure of antigenic groups. The solids are separated from the mixture, suitably by centrifugation, the water and solvent layers being discarded. The temperature should not exceed about +4° C.

The recovered solids are lyophilized and the lyophilized tissue powder is ground, as in a stainless steel ball mill, at a low temperature, preferably below about 0° C. and suitably at a temperature below about −70° C. The grinding results in a fine, grayish-brown powder.

If desired, the resulting powder is extracted with a salt solution, such as saline, at neutral pH at low temperature, suitably about 0° C, the supernatant after centrifugation being discarded. The resulting sediment may be resuspended in cold water, the sediment being recovered and lyophilized. The resulting powder may be stored for years in closed bottles at about 4° C.

When extracting the above polypeptide-containing tumor and normal powders with $H_2$ at an alkaline pH the extracts become turbid upon the addition of NaCl at neutral or slightly alkaline pHs. This turbidity is due mainly to the presence of impurities of nucleic acid character. After centrifugation of the saline-treated extracts all activity remains in the clear supernatant. The supernatant may be precipitated iso-electrically at acidic pH, suitably about 4.8, and the resulting precipitates are dissolved in an aqueous phosphate buffered solution of pH about 7.0.

The solutions resulting from the above procedure are filtered with a suitable molecular sieve type gel in bead form permitting fractionation of compounds having a MW range including $10 \cdot 10^6$ to $20 \cdot 10^6$, especially abut $15 \cdot 10^6$, the filtering gel being eluted with a buffer of about neutral pH and the MW fraction $10 \cdot 10^6$ to $20 \cdot 10^6$, especially about $15 \cdot 10^6$ being recovered. The gel or sieve may be selected from polyacrylamide gels, cross-linked dextran gels, agar and agarose gels and equivalent gels or molecular sieves, such as Bio-Gel A-50m (Trade name for an agarose gel from Bio-Rad Laboratories, Munich, West Germany; 100–200 mesh, exclusion limit (Daltons) $50 \cdot 10^6$, fractionation range (Daltons) $10^5$ to $50 \cdot 10^6$, appr. content of agarose 2%) or Sepharose 2B (Trade name for an agarose gel from Pharmacia Fine Chemicals, Uppsala, Sweden; 60–300 microns, beads, fractionation range $10^5$ to $20 \cdot 10^6$, appr. agarose content 2%), the gel being equilibrated with a suitable buffer solution at pH about 7.0, such as Sörensen's buffer (a 1/15 M buffer solution based on sodium and potassium phosphates) diluted 1:10. The type of sieve or gel used for this gel filtration is not critical and the only requirement in this regard is that is should have the ability of providing fractionation of compounds within the above-identified molecular weight range. Another useful gel for the purpose of the invention is Bio-Gel A-150m, (Bio-Rad Laboratories; 100–200 mesh, exclusion limit (Daltons) $150 \cdot 10^6$, fractionation range (Daltons) $10^6$ to $>150 \cdot 10^6$). For further details on gel filtration technique see H. Determann "Gelchromatographie", Springer-Verlag, Berlin.Heidelberg.New York 1967.

The eluant used for the filtration is a buffer solution of pH about 7, and in the effluent the antigen activity is found in the fraction containing said MW range, said fraction being recovered.

The sedimented active fractions from the above gel filtration is dissolved in a suitable buffer of pH about 7.0, such as Sörensen's buffer diluted 1:10, and the resulting solutions are filtered through a column loaded with a weak ion exchanger molecular sieve type gel having weak ion exchanging propertites, for instance a polyacrylamide gel, such as Bio-Gel P-2 (defined below), the column being equilibrated with a similar buffer of pH about 7.0. The fraction showing antigen activity is found to be the first fraction of the solution leaving the column, said fraction being recoverd.

The recovered fraction from the chromatography on Bio-Gel P-2 above is subjected to a particular procedure developed for the purpose of further purification of the CAPA. In principle, this procedure comprises the following steps: A mixture of proteins or conjugated proteins is precipitated by isoelectric adjustment of pH. The precipitate hereby obtained is mixed with a suitable gel selected while considering the protein mixture at hand. The resulting mixture of precipitate and gel is layered on top of a column containing an identical gel of the same isoelectric pH, i.e. the pH which is isoelectric for the proteins to precipitate same in the previous step. The column is then subjected to elution under gradually increasing or decreasing pH. In the eluate the fraction or fractions recovered are those containing the desired protein or proteins. Although the process of the invention is not to be bound by any particular theory it is believed that the separation of molecular species of the protein mixture can be explained in the following way:

The precipitated proteins are exposed to a flow of ions which brings one rotein after another in solution. The time required for solubilization of the various proteins will depend on the ionic strength, pH, temperature, and the flow rate. Since the distribution coefficient of each dissolved protein is lower than that of the ionic gradient, the protein will travel faster in the gel than will the gradient. In consequence, the protein will reprecipitate and become stationary until redissolved by the approaching ionic front. This process repeats itself an indefinite number of times, thus effecting separation of molecular species differing only slightly from each other.

Bio-Gel P2 is a crosslinked polyacrylamide (100–200 mesh) having a molecular weight exclusion limit of about 2000, but this exclusion limit is not critical. Other useful gels are cross-linked gels, such as Sephadex G-25, which has a molecular weight exclusion limit of about 25,000, but this exclusion limit is not critical. These gels are of the molecular sieve type and are as usual employed in bead form. Any such molecular sieve type gel having molecular weight exclusion limits of at least about 2–3000 may be employed satisfactorily. For a review of molecular sieve type gels suitable for gel filtration in combination with gradient elution, in accord with the invention, see Gellotte, Fractionation of Proteins, Peptides and Amino Acids by Gel Filtration, in "New Biochemical Separations", Van Nostrand, London/New York 1964.

The norml and CAPA fractions recovered from the chromatography above are subjected to active substance precipitation at pH about 5, the sediment being recovered and dissolved in water having a pH of about 8.5. The pH of the clear solutions is then brought to an acidic pH, suitably about 5.0 with formic acid, this treatment resulting in precipitation. Each precipitate is mixed with a slurry of a similar gel as above equilibrated with HCOOH—HCOONH$_4$ at a pH of about 5.0. Each of these mixtures is placed on top of a gel column equilibrated as above.

For the elution of the precipitates a pH gradient was used, in this case having a progressively decreasing pH. A suitable fubber system is HCOOH—HCOONH$_4$ and NH$_4$HCO$_3$—NH$_3$. The antigen activity is found in the effluent within the pH range from the initial pH to about 3.

The effluent fraction recovered within the above-identified pH-range contains the desired CAPA, which may be recovered by freeze drying. In order to establish the molecular weight of the CAPA of said effluent fraction the fraction may be subjected to filtration on a gel column equilibrated with HCOOH—HCOONH$_4$ at a pH of about 3.0, the gel being selected from those mentioned above, Bio-Gel P-30 (Trade name for a polyacrylamide gel from Bio-Rad Laboratories, Munich, West Germany; 100–200 mesh exclusion limit (Daltons) 40,000, fractionation range (Daltons) 2,500–40,000), and Sephadex G-75 or G-50 (Trade names for dextran gels from Pharmacia Fine Chemicals, Uppsala, Sweden; 40-120 and 50–150 microns, fractionation range 3–70,000 and 1–30,000, respectively) being particularly suitable gels for carrying out this filtration. The eluted fractions of CAPA having a spectrophotometric absorption peak wavelength within the range about 229 to about 233 nm and a molecular weight of from about 20,000 to about 27,000 are recovered.

The CAPA may be recovered from the active fraction after filtration by freeze drying and may be stored for a long time in vacuum, cold and in the dark.

The isolated material consists of a polypeptide based on a single chain as shown by treatment with performic acid. The CAPA shows basic reaction and is soluble at a pH within the range of about 1–3.5. The unprotected polypeptide denaturates irreversibly at neutral pHs, namely at pHs exceeding about 4.5. The antigen is hygroscopic, turns yellow and becomes inactivated and smeary when it takes up moisture.

The purified CAPA contains a fluorescent group, said group being subject to activation at a wavelength of about 288 nm while emitting light at a wavelength of about 350 nm. The fluorescence is proportional to the CAPA quantity and may be used to determine the presence of polypeptide during the procedure for its isolation.

The CAPA shows spectrophotometric peak absorption at a wavelength within the range from about 229 to about 233 nm. Moreover, it shows great tendencies to aggregation and is not filtratable on normal filter used for sterilization. It has been established that the CAPA originates from the cancer cell walls, since antibodies generated by injecting the CAPA into a living animal body cause complete lysis or decomposition of cancer cells in vivo when such cells are subjected to the effect of such antibodies.

As indicated above the polypeptide has a molecular weight within the range 20,000 to 27,000, more particularly about 24,000. Analyses indicate that it does not contain any carbohydrate and spectrophotometry indicates that the CAPA is free from nucleic acids. Analyses made with amino acid analyzer with and without oxidation indicate agreement with the molecular weight as estimated by the gel filtration on Bio-Gel P-30 or its equivalent.

The isolated CAPA may be used in many applications, such as in the preparation of monospecific antibodies, for diagnostic purposes, for immunization procedures, as an active ingredient in compositions useful as immunizing agents.

In connection with the preparation of antibodies monospecific with regard to the cancer associated polypeptide antigen, a new process has been developed. As indicated above the unprotected CAPA denaturates irreversibly at neutral pHs, which means that injecting an acidic solution of the CAPA into a living animal body results in denaturation of the CAPA immediately when it comes into contact with the neutral body fluids. In order to prevent such denaturation an oil emulsion is prepared, wherein an aqueous solution of the CAPA at a pH within the range from about 2 to about 3 constitutes the enclosed phase surrounded by the oil phase. On injecting such oil emulsion into a living animal body the acidic aqueous solution of the CAPA is protected by the surrounding oil phase when it comes into contact with the neutral body fluids. In this way the CAPA maintains its activity in vivo and may be carried to the antibody-producing cells.

An approach of maintaining antigen activity in vitro at neutral pHs resides in complexing the CAPA with inert protein, such as human or bovine albumin. By making use of such approach a complex is formed which is soluble at neutral pHs while maintaining the antigen activity in vitro.

With regard to cancer diagnosis a modified hemagglutination inhibition technique has been developed. This technique enables determining the presence of CAPA at different stages of cancer progress by investigating materials of interest, such as patient sera, tissues, secretions and extracts from living animal bodies including e.g. biopsy material, surgical specimens, punctions and smears. This new modified hemagglutination inhibition technique resides in a method comprising the steps:

(a) preparing a series of samples of the material subject to investigation by serial dilution;

(b) adding to each of said samples a predetermined amount off antiserum containing antibodies specific to the CAPA;

(c) adding, after incubation, to each of said incubated samples a predetermined amount of CAPA supported by a particulate carrier;

(d) comparing the resulting series of treated samples with a row of control samples of decreasing known amounts of CAPA providing inhibition and predetermined amounts of antiserum containing said antibodies and thereafter adding to each of said control samples a predetermined amount of CAPA supported by a similar particulate carrier; and (e) establishing by comparison of said sample series and said control sample row the amount of CAPA in the material investigated to find out the presence of cancer and its state of progress.

The invention also provides for a composition useful as an immunizing agent active in vivo, said composition comprising the CAPA as defined herein together with a pharmaceutically acceptable carrier.

The invention will now be further described by means of the following non-limiting examples.

EXAMPLE I

Isolation of Pure Antigen

Since it has been shown (Int.Arch.Allergy 36; 191–203 (1969), "Systematic Antigenic Change in Human Carcinoma Tissues by Hemagglutination Techniques", by B. Björklund) that most cancer tissue contains the antigen of this invention, cancer tissues of various types and from various sites were collected to make up a tumor pool. In this case the pool was made up from macroscopically pure, histologically verified carcinomatous tissues from the following organs (autopsy): Breast, bronchus, caecum, colon, duodenum, gall bladder, kidney, larynx, liver, lung, oesophagus, ovary, pancreas, rostate, rectum, stomach, uterus. Normal tissues were collected from a number of individuals to establish a pool of isoantigens, tissue antigens and individual antigens. Autopsy cases were used and the tumor diagnoses were histologically verified. Moreover, it was established that the pertinent tumor antigen was intact because of immunologicall cross-reactivity with fresh tumor tissues and live tumor cells. Aseptic precautions were maintained wherever possible.

The carcinomatous and normal tissues from autopsies were separately trimmed clean of adjacent tissue and cut in 2–3 cm cubes which were washed in 0.9% NaCl at 0° C. until they no longer gave off blood stain. The washed cubes were frozen and stored at −24° C.

While still in the frozen state, the tissue cubes were mixed with 10 ml $H_2O$ at 0° C for each gram of frozen tissue and homogenized in a chilled MSE Ato-Mix homogenizer with rotating knives at "half-speed" for three periods of one minute. In this connection it should be observed that the temperature of the suspension should be kept at about 0° C, preferably slightly below said temperature.

The cold homogenate was poured into cold 1000 ml polythene bottles. 400 ml suspension and 400 ml ethylether at −20° C. ("Aether ad narcosin PH Nord.", cont. diphenylamine 0.002%, from Skånska Bomullsk-rutfabriken AB, Dösjebro Sweden) were mixed in each bottle and agitated at −2° C. for 120 minutes in an International PR-2 centrifuge shaking-attachment at motor speed 300 PRM. The mixture was centrifuged at 1000 × G at +20° C. for 5 minutes. During this step the lipid layer does not mix with the tissue layer. The ethyl ether and the lipid were discarded and a second extraction was carried out for 60 minutes followed by centrifugation for 5 minutes and removal of ether-lipid layer. Finally, centrifugation at 1000 × G at +2° C. was carried out for 30 minutes and the water layer was removed although it contained some CAPA. The remaining insolubles were saved. The residual ethly ether was removed by application of vacuum for 5 minutes.

The antigenic material was suspended in 50 ml $H_2O$ at 0° C., transferred to 500 ml infusion bottles and shell-frozen at −70° C. (dry ice and ethanol).

Lyophilization was carried out in a Texvac, Type IV A lyophilizer (Textor, Bad Soden, Taunus, West-Germany), at controlled temperature.

The lyophilized tissue powder was ground in a stainless steel ball mill ("Cytolator", Lars Ljungberg Company, Stockholm, Sweden) at a temperature of about −70° C. for 2 hours at 40 RPM. The grinding resulted in a fine, grayish-brown powder. This powder was extracted with pre-chilled ethylether at −2° C. in a PR-2 shaking device at 300 RPM for 60 minutes and centrifuged at 1000 × G at −2° C. for 30 minutes. The ether layer was removed and the sediment was dried in vacuo. The resulting crude tissue powder (CTP) can be stored for years at 4° C. in closed bottles without appreciable loss of activity.

Five grams of CTP were suspended at neutral pH in 500 ml of saline containing sterile cubes of ice. The suspension was homogenized in a MSE Ato-mix at "half speed" for 3 periods of 1 minute. The temperature was kept at 0° C. The mixture was kept at 0° C. for 30 minutes at slow stirring. Centrifugation was carried out at 1000 × G at 0° C. for 40 minutes. The supernatant was discarded.

The sediment was resuspended in 500 ml cold distilled water and stirred slowly at 0° C. for 30 minutes. Following centrifugation at 1000 × G at 0° C. for 40 minutes, the supernatant was discarded. The remaining sediment was suspended in 25 ml cold distilled water and shell-frozen at −70° C. (dry ice and ethanol). Lyophilization resulted in a washed tissue powder (WTP) which can be stored for years in closed bottles at 4° C.

Aqueous extracts of CAPA and normal WTP at pH 9.5 were made and concentrated ten times by isoelectric precipitation at pH 4.8 and dissolving the precipitate in one tenth of the volume of water of pH 9.5. The resulting concentrate is stabilized by rapid heating to a temperature of 95°–100° C., preferably and, maintaining said temperature for 5–10 minutes. This heat treatment destroys enzymes, which otherwise would inactivate the CAPA. The stabilized extract became turbid upon the addition of saline at pH 7.5 due to precipitation of remaining contaminants of nucleic acid character. To precipitate such remaining contaminants 8.0 ml of CAPA and normal aqueous extracts were separately precipitated by the addition of 0.8 ml 10% solution of NaCl. After centrifugation at 27,000 × G at 0° C. for 1 hour, the clear supernatants were precipitated iso-electrically at pH 4.8 (pH adjustment with 0.1 N HCl or 0.1 N HCOOH). The precipitates were dissolved in 2–3 ml M/150 phosphate buffer, pH 7.0.

The resulting solutions originating from tumor and normal WTP were filtered with Bio-Gel A-50m (as hereinbefore defined) in refrigerated columns having an inner diameter of 2.50 cm and a length of 138 cm, at a flow rate of 6.3 ml/$cm^2$/h. The gel was equilibrated with M/150 phosphate buffer of pH 7.0 with 2% N butanol and eluted with the same buffer. In each run, 4–8 ml of extract, containing a total amount of 50–100 mg of protein were used.

The antigen activity was found in the mid-fraction of the effluent of the tumor extract. 1.0 ml aliquots of this fraction, totalling 160–180 ml. were diluted three times and adjusted to various pH-values ranging from 2.0 to 9.0. After 5 minutes at room temperature the samples were transferred to cuvettes and their light scatter at 500 nm was measured at an angle of 90°. The scatter intensities plotted against pH indicated a maximum at pH 4.8, said pH being the iso-electric point of the fraction. This method is a new technique developed for the purpose of determining the exact and necessary conditions for the purification of the CAPA. Conventional technique for the determination of the iso-electric point cannot be used here in view of the low concentration of peptide.

The remaining part of the active mid-fraction was precipitated at pH 4.8 with the aid of 0.1 N HCl. Centrifugation at 3,800 × G at 0° C. for 5 minutes resulted in a quantitative yield of activity.

To effect further purification of the CAPA the sedimented, active mid-fractions from five Bio-Gel A-50m columns were dissolved in M/150 phosphate buffer solution of pH 7.0 (Sörensen's buffer in 2% N-butanol) to 5% of the original effluent volume. This solution containing 130 mg protein in 8.5 ml was filtered through a Bio-Gel P-2 column (as hereinbefore defined) with a ratio diameter/height of 1/35 and at a flow rate of 35 ml/cm$^2$/h. The column had been equilibrated with M/150 phosphate buffer of pH 7.0 (Sörensen's buffer in 2% N-butanol). For each mg of protein a bed volume of 10 ml was permitted.

The first fraction was active and was excluded with the eluting buffer of pH 7.0 while impurities were absorbed on the gel at the low ionic strength used. The active substance was precipitated at pH 4.8 with 0.1 M HCOOH and centrifuged at 3,800 × G at 0° C. for 5 minutes. The sediment was dissolved in 8.5 ml H$_2$O and the pH adjusted to 8.5 with 0.1 M NH$_4$OH. The clear solution was reprecipitated three times with 0.1 M HCOOH at pH 4.8, washed in the centrifuge at the same pH and dissolved at pH 8.5. The disappearance of N-butanol was followed by gas-liquid chromatography. The final solution was stored in ampoules, shell-frozen and lyophilized. The resulting product was a dry, almost white powder and this powder was stored at −24° C. in the evacuated and sealed ampoules.

An identical procedure was employed with a corresponding extract originating from normal tissue and no activity was found.

For further purification of the product obtained from the previous chromatographic procedure, a pH gradient elution process was developed. This process resides, in principle, in the following steps: Protein mixture to be purified with regard to the active component thereof is precipitated by an isoelectric adjustment of pH. The precipitate is mixed with a suitable gel, such as Sephadex G-25 (as hereinbefore defined) or Bio-Gel P-2 (as hereinbefore defined). This mixture is layered on top of a column containing an identical gel of the same isoelectric pH. The column is then subjected to pH-gradient elution under constant flow rate and temperature. Thus, the column is eluted with a medium of continuously or stepwise increasing or decreasing pH.

The instant case gradient elution was carried out with 15 mg of lyophilized and salt-free CAPA powder and normal antigen powder purified as described in the preceding section, in this case by decreasing pHs. The powders were separately dissolved in H$_2$O, the pH being adjusted to 8.5 with 0.1 N NH$_4$OH. The pH of the clear solutions was then brought to 5.0 with 0.1 M HCOOH which resulted in precipitation. Each precipitate was mixed with 10 ml Bio-Gel P-2 slurry equilibrated with an aqueous solution prepared from 0.02 M HCOOH and 0.02 M HCOONH$_4$ to make a pH of 5.0. Each of these mixtures was placed on top of a 15 ml Bio-Gel P-2, silicon-treated column, having an inner diameter of 16 mm and a length of 150 mm, equilibrated as above. The gel was supported by a small piece of glass-wool.

A pH-gradient was used for elution of the precipitates. By means of a gradient mixer (Ultrograd,LKB, Sweden) the pH was kept at about 5 for a short period of time to wash the precipitate and then the pH was gradually lowered to 2.8. Finally, the pH was raised to 9. The buffer system comprised 0.02 M HCOOH—HCOONH$_4$ and 0.02 M NH$_4$HCO$_3$—NH$_3$ and the elution was made at room temperature. The flow rate was held at 27.2 mls per square cm column cross-section per hour.

The effluent from the tumor extract was assayed by fluorescence spectrometry (activation at 288 nm, fluorescence emitted at 350 nm). The fraction eluted between the initial pH and about 3 was recovered for further use. After lyophilization and freeze-drying the product could be stored in sealed ampoules after removal of air at −24° C.

For characterization of molecular size and to confirm the purity, the antigenic material in the form of solutions thereof were filtered with Bio-Gel P-30 (as hereinbefore defined) which had been equilibrated with a buffer 0.02 M HCOOH—HCOONH$_4$, pH 3.0. The pH-eluted CAPA was dissolved in a small amount of the same buffer. The flow rate was 3.25 ml/cm$^2$/hour and the fractions collected comprised 1.24 ml. The active fractions showed a spectrophotometric absorption maximum at a wavelength of 229–233 nm and a fluorescence of 350 nm when activated at 288 nm.

In a typical run, 10.4 mg of CAPA dissolved in 3.0 ml of the above buffer on a siliconized Bio-Gel P-30 column (i.d. 2.54 cm, length 50 cm), resulted in complete recovery of both substance and activity. The elution volume was compatible with a MW within the range 22,000–24,000. These molecular weight figures were obtained by comparing the elution volumes with those of compounds of known MWs, such as ribonuclease and insulin. After freeze-drying there is obtained a white hygroscopic powder which can be stored in the cold and in the absence of light and oxygen. Upon analyzing the product, no carbohydrate and no nucleic acids are found. Analyses by amino acid analyzer indicated agreement with molecular weight as estimated by gel filtration. Analyses of the amino acids show the following mole percentages, the figures being of an accuracy of ± 5%: The calculated molecular weight was 23,200 ± 2,500 (Standard deviation).

| Alanine | 8.62 |
| --- | --- |
| Arginine | 4.57 |
| Aspartic acid | 10.39 |
| Cysteine | 0.95 |
| Glutamic acid | 17.04 |
| Glycine | 6.87 |
| Histidine | 1.00 |
| Isoleucine | 4.75 |
| Leucine | 10.49 |
| Lysine | 3.69 |
| Methionine | 1.91 |
| Phenylalanine | 2.75 |
| Proline | 3.79 |
| Serine | 7.74 |
| Threonine | 5.92 |
| Tyrosine | 3.21 |
| Valine | 6.36 |

This amino acid content corresponds to a theoretical nitrogen content of 16.2–17.8%. Determination of total nitrogen according to Dumas' points to a value of 17.0 ± 0.5%. As shown by treatment with performic acid the polypeptide is based on a single peptide chain. Moreover, the polypeptide, if not protected by complexing with albumen, denaturates irreversibly at pHs exceeding about 5.

EXAMPLE Ia

In exactly the same manner as described in Example I above the polypeptide is prepared from human placenta tissue.

EXAMPLE Ib

Preparation of CAPA-albumen Complex

An aliquot of the CAPA as prepared under Example I is dissolved in formic acid (for instance 0.05M; the pH should be within the range 2–3). A clear solution is obtained. To said solution there is added albumen powder or a solution of albumen at the same pH as of the above formic acid solution (200 parts by weight of albumen per 1 part by weight of CAPA) resulting in a clear solution of CAPA and albumen. Then the pH of the solution is slowly increased by adding a base (for instance an aqueous sodium hydroxide solution or ammonia) until pH reaches about 7.5. This results in a clear solution containing CAPA and albumen in the form of a complex.

This solution containing 12 $\mu$g CAPA/ml may be used directly in the diagnostic procedure described below or the complex may be isolated in the form of a white powder by freeze-drying. The powder is stable in the cold (+4° C.) for a long period of time.

It has been shown by experiments that maximum utilization of the CAPA activity is obtained at a weight ratio of albumen to CAPA equal to about or exceeding 200:1.

EXAMPLE Ic

Preparation of Tanned and Labelled Red Blood Cells

Fresh sheep blood (1 part by volume) are added to sterile Alsever's solution (1.2 part by volume)(Alsever's solution is prepared from 250 g glucose, 80 g sodium citrate dihydrate, 42 g NaCl, add water to make up to 10 liters, pH adjusted to 6.1 with 10% citric acid monohydrate). The mixture is centrifuged and the red blood cells are resuspended once in Alsever's solution and twice in a buffer solution of pH 6.8. Finally, a suspension of the red blood cells is made up in the buffer 6.8 at a concentration of $10^9$ cells/ml.

1 Volume of red blood cell suspension prepared as above is added to 1 volume of buffer solution of pH 6.8 containing about 18 $\mu$g tannic acid/ml under stirring. The thus tanned red blood cells are centrifuged and resuspended twice in buffer of pH 7.5. Finally, the red blood cells are suspended in buffer of pH 7.5 at a concentration of $10^9$ cells/ml.

An aliquot of the CAPA complex prepared under Example Ib above is dissolved in a buffer solution of pH 7.5 to give a concentration of 3 $\mu$g CAPA per ml (calculated on pure CAPA). 1 part by volume of the suspension of tanned red blood cells prepared above is added dropwise at 0° C. to 1 part by volume of the CAPA complex solution for a period of time of 10 minutes. The labelled cells are centrifuged and resuspended in a buffer solution of pH 7.5 containing a stabilizing amount (about 1.2 volume/volume) of inert human serum to give a suspension containing $1.6 \times 10^8$ labelled cells per ml. These labelled cells are used as shown below in the diagnostic procedure of the invention.

EXAMPLE II

Preparation of Antibodies

In view of the fact that the CAPA of the invention denaturates irreversibly at neutral pHs as hereinbefore indicated, it was suspected that parenteral injection of the polypeptide would not result in the production of antibodies. Experiments carried out on rabbits confirmed this and it was found that no antibody production occurred after the injection of polypeptide complexed with albumen into rabbits. All hemagglutination reactions were negative.

In order to be able to transfer the polypeptide in an active condition to the antibody producing cells it is necessary to maintain the polypeptide in the solution at pHs lower than about 3 (0.02 m HCOOH, pH 2.8) and to emulgate the solution in oil to the formation of extremely small drops surrounded by a protecting oil layer. The injection of the emulsion resulted in production of satisfactory quantities of antibodies, which reacted specifically with the CAPA in hemagglutination reactions, wherein blood cells had been labelled with CAPA.

Preparation of Immunizing Agent

816 Micrograms of pure CAPA prepared from pooled human cancer tumors were dissolved in 1.0 ml 0.02 m HCOOH of pH 2.8. To the resulting solution there was added dropwise 1.0 ml adjuvant oil (commercial preparation from Difco Laboratories, Detroit, Michigan, USA; Bacto-Adjuvant, Freund) under simultaneous emulsification. The emulsification was carried out according to Freund by means of an injection syringe, the mixture being drawn up and down in the syringe to the formation of a uniform, white emulsion having about the same consistency as whipped cream. One drop of said emulsion was tested with ice water to confirm that it floated separately and maintained intact. The resulting, semi-liquid emulsion was used for subcutaneous and intramuscular injections on rabbits.

Immunization of Five Rabbits

In the first injection a so-called complete adjuvant was used and in the subsequent injections a so-called incomplete adjuvant was used. After initial drain of blood from each of five rabbits to establish O-values, totally 408 micrograms of emulsified CAPA at pH 2.8 were injected subcutaneously on each right and left hand side. At ten day intervals additionally three injections were given, the first one intramuscularly in each hind leg and the second and the third subcutaneously on both front sides and both backs, respectively. The selection of the injection sites was made in order to utilize the admission areas of the regional lymphatic glands. In total, each rabbit received about 1.6 mgs of CAPA in the form of emulsion. 14 and 24 days after the last injection test samples of blood were taken, which were subjected to hemagglutination analysis with regard to the presence of specific antibodies against CAPA. Two days after the last sample a maximum amount of blood was drained, which was recovered in the form of serum that was sterile filtered and transferred in small portions to sterile tubes. These tubes could be stored in the cold while maintaining the specificity.

EXAMPLE III

Diagnostic Procedure (a) Single Blind Study

Blood samples were obtained from the Central Hospital of Eskilstuna, Sweden, of which 42 originated from patients of the infection clinic; one from the surgical clinic; two from radiotherapy; ten from post partus women; ten from umbilical cord blood and ten from women pregnant in 1-trimester and six in 2-trimester. Moreover, blood was obtained from twenty 10 year old children from Slottsskolan and ten samples from older healthy adults from the private clinic of Dr. Lundström in Eskilstuna, Sweden. From the surgical and medical clinics of Ersta Sjukhus in Stockholm, Sweden, there were obtained samples from forty-four patients, from Åkeshovs Hospital, samples were obtained from forty-five patients and from the surgical clinic of Karolinska Sjukhuset in Stockholm, Sweden, there were obtained blood samples from seventy-two patients admitted for possible surgery. The Blood Donor Department of Karolinska Sjukhuset in Stockholm, Sweden, provided 118 samples from donors of ages ranging from 20–67 years, average age 37.2 years (SD ± 11.3 years), and from the Clinical Central Laboratory of said hospital sera were obtained from 29 patients subject to care within the general divisions of Radiumhemmet in Stockholm, Sweden, and from twelve patients within its gynaecological divisions.

The total number of blood samples was 431. With regard to the 111 cases from Eskilstuna a clinical investigation was made and a medial record was drafted except for the participants of obvious health. As regards the Stockholm cases, detailed studies of patients' medical records were made with regard to 101 cases. In the remaining cases other clinical diagnoses than malignancy were at hand and there was no suspicion of malignant disease.

Venous blood was transferred to Wassermann tubes without additive and was transferred to the laboratory, in some cases after the removal of coagulum and blood cells by means of centrifugation.

The blood analysis was based on indication of the existance of CAPA by means of a modified hemagglutination inhibition technique (micromethod). In principle, the following procedure was used:

25 μl of patient serum, which had been absorbed with sheep red cells, was titrated in 8 steps 2-dilution in Linbro IS-MCR-96 dilution plates, and then 25 μl of specific antiserum in limit dilution (about 1:2000) was added to each cavity. After incubation at 22° C. for 10 minutes there was added to each cavity 50 μl of a suspension of about 6–8 million sheep blood red cells tanned and labelled with isolated CAPA linked to human albumen as shown under Example Ic above (about 2–4 μg per $10^9$ blood cells). Other particulate carriers, such as latex, bentonite, and collodion, can be employed instead of the red blood cells. The reaction was recorded by means of an inclined mirror and a standard series after 4–24 hours incubation at 1°–2° C. For control purposes, use was made of:

1. CAPA labelled blood cells plus antiserum;
2. CAPA labelled blood cells without antiserum;
3. Patient serum plus blood cells labelled with human albumen;
4. Patient serum and untreated blood cells;
5. CAPA labelled blood cells and antibodies in one row where inhibition is provided by stepwise decreasing known amounts of CAPA.

The dilution liquids used contained pooled (i.e. combined from many individuals) inactivated neutral human serum for the stabilization of the blood cells.

CAPA-reagent was prepared from pooled human carcinoma tissues and was purified as described above by means of gel filtration, pH-gradient elution, filtering through Bio-Gel P-30 and complexing with albumen.

As antiserum there was used horse anti-HeLa from Nov. 19, 1962, absorbed by normal tissues and pooled human serum. The immunization was made with washed fragments of HeLa-cells grown in Eagle's medium containing 20% inactivated human serum in flat glass bottles. The cells had been harvested with EDTA, centrifuged and washed three times with water.

In the presence of CAPA in patient serum, the horse antibodies were neutralized resulting in the absence of agglutination when the polypeptide labelled blood cells were subsequently added. Recording was made after an increasing score from 0–6, wherein 0 indicates absence of inhibition and 6 indicates maximum inhibition of the agglutination. The relation between the scores and the concentration of CAPA per ml of serum is seen from Table 1 obtained by calibration of dilutions of predetermined amounts of CAPA in neutral serum.

Table 1.

| Approximative calibration of scores and quantity of CAPA. | |
|---|---|
| Score | μg CAPA/ml |
| 0 | ≦0.03 |
| 1 | 0.04 – 0.08 |
| 2 | 0.09 – 0.12 |
| 3 | 0.13 – 0.24 |
| 4 | 0.25 – 0.49 |
| 5 | 0.50 – 0.99 |
| 6 | ≧ 1.0 |

The recordings were made without knowledge of the health conditions of the patients. The material subject to investigation has been grouped as seen from Table 2 below.

Table 2.

The presence of CAPA in 431 sera from individuals of different groups according to an integer score from 0 to 6 and average scores (M) and standard deviations (SD).

| | Groups | Integer score | | | | | | | Number | M ± SD |
|---|---|---|---|---|---|---|---|---|---|---|
| | | 0 | 1 | 2 | 3 | 4 | 5 | 6 | | |
| 1. | Primary cancer with metastases | | | 5 | 4 | 1 | 2 | | 12 | 3.00 ± 1.13 |
| 2. | Extended cancer | 4 | 2 | 1 | 4 | 8 | 2 | 1 | 22 | 2.91 ± 1.82 |
| 3. | Cancer not radically treated | 6 | 10 | 15 | 8 | | | | 39 | 1.64 ± 0.99 |
| 4. | Primary cancer untreated | 3 | 1 | 4 | 2 | | | | 10 | 1.50 ± 1.18 |
| 5. | Cancer radically removed | 19 | 1 | 1 | | | | | 21 | 0.14 ± 0.19 |
| 6. | Malignant disease other than cancer | 7 | 3 | 1 | | | | | 11 | 0.45 ± 0.68 |
| 7. | Non-malignant disease | 118 | 3 | 3 | 7 | 1 | | | 132 | 0.26 ± 0.22 |

Table 2.-continued

The presence of CAPA in 431 sera from individuals of different groups according to an integer score from 0 to 6 and average scores (M) and standard deviations (SD).

| | Groups | Integer score | | | | | | | Number | M ± SD |
|---|---|---|---|---|---|---|---|---|---|---|
| | | 0 | 1 | 2 | 3 | 4 | 5 | 6 | | |
| 8. | Healthy adults (M = 71 years) | 8 | 2 | | | | | | 10 | 0.20 ± 0.42 |
| 9. | Blood donors (M = 39 years) | 116 | 2 | | | | | | 118 | 0.02 ± 0.13 |
| 10. | 10-year old individuals | 19 | | 1 | | | | | 20 | 0.10 ± 0.44 |
| 11. | Newly born (umbilical cord blood) | 1 | 1 | 1 | 4 | 2 | 1 | | 10 | 2.80 ± 1.48 |
| 12. | Pregnant women | 12 | 2 | 2 | | | | | 16 | 0.38 ± 0.72 |
| 13. | Women post partus | 8 | 1 | | 1 | | | | 10 | 0.40 ± 0.97 |

It is clear from the results that the highest scores have been obtained with the groups comprising "primary cancer and metastases" (local) and by "extended cancer" and group "newly born" (umbilical cord blood).

Low scores have been obtained for blood donors. An intermediate position is taken by the group "Primary cancer untreated" and the group "cancer not radically treated". Scores about the same as those of the blood donors are found within the group "cancer radically removed".

The average values as to CAPA in all groups have been compared pair-wise and are shown in Table 3 below.

significantly higher relative to all groups except the two first-mentioned and relative to "malignant disease other than cancer" relative to which the difference is significant (0.01<P<0.05).

Groups 5–9 do not show mutual significant differences except for the significant difference between 7 and 9. This difference may be explained by the fact that genuine, hidden cancer cases may be present among the cases showing scores between 1 and 4.

The positive indication in umbilical cord blood deserves certain attention. In order to establish whether the CAPA originates from placenta, pieces of such tissue were extracted. Amounts of 300 mgs of frozen Table 3.

Statistic significance $^{a)}$ of differences between scores for presence in sera of CAPA of nine categories of individuals.

| | Groups | M ± SD | Significance $^{b)}$ of difference between categories number | | | | | | | |
|---|---|---|---|---|---|---|---|---|---|---|
| | | | 2 | 3 | 4 | 5 | 6 | 7 | 8 | 9 |
| 1. | Primary cancer with metastases | 3.00 ± 1.13 | 0 | XX | XX | XXX | XXX | XXX | XXX | XXX |
| 2. | Extended cancer | 2.91 ± 1.82 | | XX | XX | XXX | XXX | XXX | XXX | XXX |
| 3. | Cancer, not radically treated | 1.64 ± 0.99 | | | O | XXX | XX | XXX | XXX | XXX |
| 4. | Primary cancer, untreated | 1.50 ± 1.18 | | | | XXX | X | XXX | XX | XXX |
| 5. | Cancer radically removed | 0.14 ± 0.19 | | | | | O | O | O | O |
| 6. | Malignant disease other than cancer | 0.45 ± 0.68 | | | | | | O | O | O |
| 7. | Non-malignant disease | 0.26 ± 0.22 | | | | | | | O | XXX $^{c)}$ |
| 8. | Old healthy adults | 0.20 ± 0.42 | | | | | | | | O |
| 9. | Blood donors | 0.02 ± 0.13 | | | | | | | | |

$^{a)}$ Significance tests of differences were made by means of an approximatively normal distributed variable, Z, defined as:

$$Z = \frac{M_1 - M_2}{\sqrt{\frac{SD_1^2}{n_1} + \frac{SD_2^2}{n_2}}}$$

$^{b)}$ if Z>1.96 the significance of difference is X, which means
0.01<P<0.05
if Z>2.6 the significance of difference is XX, which means
0.001<P<0.01
if Z>3.5 the significance of difference is XXX,
P<0.001
$^{c)}$ This group includes 11 positive tests of which 8 refer to suspected but not verified cancer.

It is clear from the table above that with regard to "primary cancer with metastases" as well as for "extended cancer" there are significantly higher average scores relative to all of the other groups with the exception, however, for newly born (see also Table 2).

For the groups "cancer not radically treated" as well as "primary cancer untreated" the average scores are placenta tissue per ml buffered physiological NaCl solution at pH 7.5 were homogenised at 0° C. and centrifuged at homogenized 1000 × G for 30 minutes at 0° C. in conically extended tubes (according to Markham). The supernatants were tested for presence of CAPA by means of the hemagglutination technique described above. To exclude the possibility that the inhibition reactions obtained were caused by unspecific inactivation of the pure CAPA applied to the blood cells, said blood cells were shaken after each recording and a standard amount of antibodies specific to the CAPA was added. No antigen inactivation could be indicated in any of the cases. As control material there wa used an extract of antigen powder produced from human cancer tissues of different origin and from different localizations. The results show, that out of 26 placentas from as many individuals all without exception contained significant quantities of CAPA. The average figure (geometrical) for the 26 placentae was 297 ± 8 micrograms per gram wet tissue (0.03%).

Since as is clear from the above investigation that the CAPA of this invention is synthetized in the placenta, and since the genes contained in the placenta must be present also in the individual originating from the same ovum cell, it follows that the ability or capacity to generate the CAPA is a normal phenomenon. Normally, this capacity is repressed since normal cells do not contain the CAPA in measurable amounts. In cancer cells, however, an activation of the capacity has occurred characterized by a significant presence of CAPA within and about the cells. The antigenic and to some extent functional similarity between trophoblast cells of the placenta and cancer cells and the difference with regard to the other cells of the individual seems compatible with the view that the cancer diseases are due to changed control of inherent properties.

A statistical analysis of the experimental results shows that there is a highly significant correlation between the presence of cancer diagnosis and increased CAPA concentration ($P<0.001$). The same holds true for the relation between the size of the tumor mass considered and the increased CAPA concentration within the same age groups ($P<0.001$). The increased concentration of CAPA has been found in connection with a large variety of different localizations of cancer. Irrespective of type and localization cancer tumors have been found to contain the CAPA in view of which said CAPA seems to be common to all known types of cancer, i.e. malignant tumors of epithelial origin.

(b) Double Blind Study

In order to attest further to the validity of the above conclusions, a double blind study was performed under the most rigidly controlled conditions. Coded blood specimens were obtained from the various departments of the Central Hospital of Eskilstuna, Sweden. In this case quantitative measurements of the CAPA level of the patient's sera were made.

The results from this double blind study as well as the results from the fore-going single blind study are summarized in tables 4–8 below. In said tables:

Table 4 shows the total number of examined individuals and the number of individuals showing cancer diagnosis;

Table 5 shows the number of individuals of the different groups together with their average ages and the deviations thereof;

Table 6 shows the presence of CAPA in the sera from all examined patients;

Table 7 shows the percentages of individuals having a CAPA concentration of $\geq 0.15$ μg/ml serum while excluding groups 9, 10 and 12 of table 5.

Table 8 shows the presence of CAPA in relation to tumor localizations for groups 1–3 of table 5. The site numbers refer to "Cancer Incidence in Sweden 1968" incorporated herein by reference.

Table 4.

| Studies | Number of examined individuals. | |
|---|---|---|
| | Number of individuals | Number of individuals showing cancer diagnosis |
| Single blind | 431 | 104 |
| Double blind | 503 | 49 |
| | 934 | 153 |

Table 5

Number of individuals of different groups and average ages and deviations thereof.

| | Single blind study | | | | Double blind study | | | |
|---|---|---|---|---|---|---|---|---|
| Groups | Number | Average age | ± | Deviation | Number | Average age | ± | Deviation |
| 1. Cancer with metastases | 34 | 72 | ± | 9 | 14 | 66 | ± | 10 |
| 2. Untreated cancer without metastase indications and cancer not radically treated | 49 | 67 | ± | 11 | 14 | 66 | ± | 12 |
| 3. Cancer radically removed | 21 | 66 | ± | 15 | 21 | 64 | ± | 12 |
| 4. Malignant disease other than cancer | 11 | 70 | ± | 7 | 5 | 58 | ± | 18 |
| 5. Non-malignant disease | 132 | 61 | ± | 22 | 186 | 46 | ± | 21 |
| 6. Healthy adults | 10 | 71 | ± | 5 | 46 | 36 | ± | 14 |
| 7. Blood donors | 118 | 38 | ± | 11 | — | — | | — |
| 8. 10 year old and younger individuals | 20 | 10 | ± | 0 | 62 | 2 | ± | 1.5 |
| 9. Umbilical cord blood | 10 | 0 | ± | 0 | 20 | 0 | ± | 0 |
| 10. Women post partus | 10 | 21 | ± | 3 | 20 | 25 | ± | 4 |
| 11. Pregnant women | 16 | 26 | ± | 4 | 110 | 26 | ± | 4.5 |
| 12. Cancer in situ | — | — | | — | 5 | 27 | ± | 6 |
| Total | 431 | | | | 503 | | | |

Table 6

Presence of CAPA in sera from 934 individuals.

| Groups | CAPA ≦0.08 μg/m Number | (%) | CAPA ≧0.09 μg/ml Number | (%) | Total Number | (%) |
|---|---|---|---|---|---|---|
| 1. Cancer with metastases | 9 | (19) | 39 | (81) | 48 | (100) |
| 2. Untreated cancer without metastase indications and cancer not radically treated | 28 | (44) | 35 | (56) | 63 | (100) |
| 3. Cancer radically removed | 36 | (86) | 6 | (14) | 42 | (100) |
| 4. Malignant disease other than cancer | 15 | (94) | 1 | (6) | 16 | (100) |
| 5. Non-malignant disease | 269 | (85) | 49 | (15) | 318 | (100) |
| 6. Healthy adults | 54 | (96) | 2 | (4) | 56 | (100) |
| 7. Blood donors | 118 | (100) | 0 | (0) | 118 | (100) |
| 8. 10 year old and younger individuals | 79 | (96) | 3 | (4) | 82 | (100) |
| 9. Umbilical cord blood | 21 | (70) | 9 | (30) | 30 | (100) |
| 10. Women post partus | 25 | (83) | 5 | (17) | 30 | (100) |
| 11. Pregnant women | 123 | (98) | 3 | (2) | 126 | (100) |
| 12. Cancer in situ | 4 | (80) | 1 | (20) | 5 | (100) |
| Total | 781 | (84) | 153 | (16) | 934 | (100) |

Table 7

Percentage of individuals showing a CAPA concentration of 0.15. Groups 9, 10 and 12 of Table 5 have been excluded.

| Groups | % | Number |
|---|---|---|
| 1. Cancer with metastases | 64 | 48 |
| 2. Untreated cancer without metastase indications and cancer not radically treated | 21 | 63 |
| 3. Cancer radically removed | 10 | 42 |
| 4. Malignant disease other than cancer | 0 | 16 |
| 5. Non-malignant disease | 6 | 318 |
| 6. Healthy adults | 0 | 56 |
| 7. Blood donors | 0 | 118 |
| 8. 10 year old and younger individuals | 0 | 82 |
| 11. Pregnant women | 1 | 126 |
| Total | | 869 |

Table 8.

Presence of CAPA in relation to tumor localizations of groups 1-3.

| Localization | Site No[x)] | 1. Cancer with metastases ≦0.08 | ≧0.09 | 2. Untreated cancer without metastase indications and cancer not radically treated ≦0.08 | ≧0.09 | 3. Cancer radically removed ≦0.08 | ≧0.09 | Total |
|---|---|---|---|---|---|---|---|---|
| Gingivae mandib. | 144 | | | 1 | | 1 | | 2 |
| Nasopharynx | 146 | | | 2 | 1 | | | 3 |
| Oesophagus | 150 | | 1 | 3 | 1 | 1 | | 6 |
| Ventricle | 151 | 1 | 2 | 1 | 2 | 2 | | 8 |
| Intestinum tenui | 152 | 1 | | | | | | 1 |
| Colon | 153 | | 2 | 1 | 7 | 6 | | 16 |
| Rectum | 154 | | 4 | 1 | 5 | 3 | 1 | 14 |
| Ves.fellea,etc. | 155 | | 1 | 1 | 1 | | | 3 |
| Hepar | 156 | | 1 | | | | | 1 |
| Pancreas | 157 | | 3 | | 1 | 2 | | 6 |
| Vestibul. nasi, etc. | 160 | | | | 1 | 1 | | 2 |
| Trachea, pulm etc. | 162 | | 4 | 2 | 3 | 5 | | 14 |
| Mammae | 170 | 2 | 7 | 1 | 3 | 3 | 2 | 18 |
| Cervix uteri | 229 | | 2 | 3 | 1 | | | 6 |
| Corpus uteri | 198 | 1 | 1 | 1 | 1 | 1 | 2 | 7 |
| Ovarii, etc. | 175 | 1 | 4 | 1 | 1 | 2 | | 9 |
| Prostate | 177 | 2 | 3 | 3 | | 1 | | 9 |
| Testis | 178 | | 1 | | 1 | 1 | | 3 |
| Penis, etc. | 179 | | | | 1 | 1 | | 2 |
| Renes | 180 | 1 | | 3 | | 1 | | 5 |

Table 8.-continued
Presence of CAPA in relation to tumor localizations of groups 1-3.

| Localization | Site No[x] | 1. Cancer with metastases | | 2. Untreated cancer without metastase indications and cancer not radically treated | | 3. Cancer radically removed | | Total |
|---|---|---|---|---|---|---|---|---|
| | | ≦0.08 | ≧0.09 | ≦0.08 | ≧0.09 | ≦0.08 | ≧0.09 | |
| Ves.urinaria, etc. | 181 | | 1 | 2 | 3 | 3 | 1 | 10 |
| Malignant melanoma | 190 | | | 1 | 1 | | | 2 |
| Thyreoidea | 194 | | 1 | 1 | 1 | 2 | | 5 |
| Primary tumor origin unknown | | | 1 | | | | | 1 |
| Total | | 9 | 39 | 28 | 35 | 36 | 6 | 153 |

[x] According to "Cancer Incidence in Sweden 1968".

A thorough statistical analysis of the data obtained in this double blind study again shows the highly significant correlation between the presence of cancer diagnosis and increased CAPA concentratin ($P<0.001$). This double blind study also confirms the relation between the size of the tumor mass considered and the increased CAPA concentration within the same age groups ($P<0.001$). The increased serum level of CAPA has been found in connection with about 20 different types and localizations of cancer. Thus, the double blind study fully confirms the validity of the new findings and their practical usefulness.

In the introductory part of this disclosure it has been indicated that the antigen disclosed in U.S. Pat. No. 3,663,684 is clearly different from the antigen of this invention. To demonstrate the difference between the prior art antigen and the antigen of the invention there is given below a detailed survey on some specific differences both with regard to the process of antigen isolation and with regard to the characteristics of the antigen.

| CEA | CAPA |
|---|---|
| Source: Cancer of the colon Fetus (Mekonium, gut) | Source: All cancers, cancer cell lines in vitro, placenta. (Little if any in fetus). |
| Extraction from the antigen-containing tissues by glycoprotein solvent at low pH at room temperature: Keep extract. | Washing the tissue with water at neutral pH, extraction with ethyl ether (optional), throw away the extract, Extraction of solids at high pH (9.5), keep the extract, temperature in the water treatment: ≦ 0° C. |
| Isoelectric point: Not given or non-existing | Isoelectric point: About 5 (before final step) |
| Absorption of UV-light at 280 nm | Absorption of UV-light at 230 nm (very little at 280 nm) |
| Fluorescence: Not mentioned | Fluorescence: Activation at 288 nm Emission at 350 nm |
| Molecular weight 200,000 (may be as low as 70,000 | Molecular weight 23,200 ± 2,500 |
| Active at neutral pH | Destroyed at neutral pH |
| Contains sugar (glycoprotein) | No sugar by gas-liquid chromatography and mass spectroscopy and other analyses |
| No inhibition of antibodies to CAPA by hemagglutination Does not label sheep red cells treated with tannic acid. | Inhibits specific antibody by hemagglutination Does label such cells. |
| Is present in cancer disease | Present in serum in |

| | -continued |
|---|---|
| CEA in concentrations from some nanograms to 100-200 nm per ml | CAPA concentrations of 0.09-8 μg/ml (equivalent of 90-8,000 ng/ml), i.e. approximately 20 times higher than CEA. |
| Assay: Expensive, time-consuming, requires radioactive isotopes. | Easy, rapid, inexpensive, no isotopes, no expensive equipment required. |

To summarize there are given below brief definitions of cancer associated polypeptide antigen and the diagnostic test of this invention.

Definition of CAPA

HeLa cells (originating from a case of cancer in 1952) are grown in vitro. These cells are used as a source of antigen. The harvested cells are injected into horses resulting in the production of specific antibody which is used to identify the antigen in tumors, serum, placenta etc. The latter antigen must have and does have an identical immunological reaction site (as compared to the HeLa-antigen) but can, of course, be different in other respects when present in a natural state.

Definition of Diagnostic Test

Antigen from HeLa cell cultures in vitro is used to produce antibody in horses. After absorption of unwanted antibodies, the horse serum is used to agglutinate red cells labelled by antigen taken out of tumors (or placenta or cell cultures of HeLa or HEp-2 or Detroit-6). This is the indicator system. If an unknown sample contains antigenic activity it will interfere with the antibody and does inhibit agglutination.

Various modifications and equivalents will be apparent to those skilled in the art and can be made in the processes and the products of the present invention without departing from the spirit of scope thereof, and it is, therefore, to be understood that the invention is to be limited only by the scope of the appended claims.

Chart

Purification of tumor associated antigen

Flow chart with conditional branching illustrating the general approach of purification.

-continued

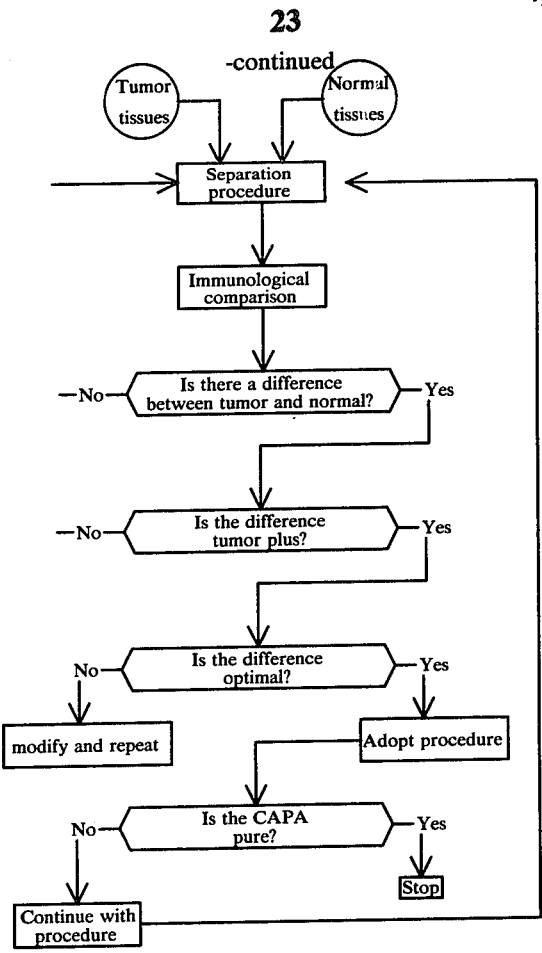

What is claimed is:

1. A method of making an antigen albumen complex comprising the steps of:
   mixing, in acid solution, at a pH not exceeding about 5, the antigen, said antigen being:
   a cancer associated polypeptide antigen, obtained from a source selected from the group consisting of human tumor tissue, a culture of cancerous cells grown in vitro, and human placental tissue, having a molecular weight of 23,200 ± 2,500 (S.D.) and showing a spectrophotometric peak absorption at a wave length within the range from about 229 nm to about 233 nm, said polypeptide being based on a single peptide chain as shown by treatment with performic acid, said single peptide chain comprising the following amino acids: Alanine, Arginine, Aspartic acid, Cysteine, Glutamic acid, Glycine, Histidine, Isoleucine, Leucine, Lysine, Methionine, Phenylalanine, Serine, Threonine, Tyrosine, and Valine, said polypeptide antigen comprising also a fluoroescent group which emits fluorescent light at about 350 nm when activated at a wavelength of about 288 nm, and, if not protected by complexing with albumen, denaturating irreversibly at pH's exceeding about 5,
   and albumen, and
   raising the pH of the solution to about neutral to cause interaction between the components and production of a relatively stable antigen albumen complex.

2. A method according to claim 1, including the further step of lyophilizing the complex.

3. A complex, useful as a stabilized antigen for diagnostic purposes, comprising:
   a cancer associated polypeptide antigen, obtained from a source selected from the group consisting of human tumor tissue, a culture of cancerous cells grown in vitro, and human placental tissue, havng a molecular weight of 23,200 ± 2,500 (S.D.) and showing a spectrophotometric peak absorption at a wave length within the range from about 229 nm to about 233 nm, said polypeptide being based on a single peptide chain as shown by treatment with performic acid, said single peptide chain comprising the following amino acids: Alanine, Arginine, Aspartic acid, Cysteine, Glutamic acid, Glycine, Histidine, Isoleucine, Leucine, Lysine, Methionine, Phenylalanine, Serine, Threonine, Tyrosine, and Valine, said polypeptide antigen comprising also a fluoroescent group which emits fluorescent light at about 350 nm when activated at a wavelength of about 288 nm, and if, not protected by complexing with albumen, denaturating irreversibly at pH's exceeding about 5,
   and a stabilizing amount of albumen complexed therewith by the method of claim 1.

4. The complex of claim 3, wherein the ratio of albumen to the antigen, is equal to about or exceeding 200:1 by weight.

5. A diagnostic composition comprising a particulate material labelled with the albumen-stabilized antigen of claim 3.

6. The diagnostic composition of claim 5, wherein the particulate material is selected from the group consisting of tanned red blood cells, latex bentonite and collodion.

* * * * *

UNITED STATES PATENT AND TRADEMARK OFFICE
CERTIFICATE OF CORRECTION

PATENT NO. : 4,160,018
DATED : July 3, 1979
INVENTOR(S) : Knut Bertil Bjorklund

It is certified that error appears in the above-identified patent and that said Letters Patent are hereby corrected as shown below:

Col. 1, line 5; "filled" should read -- filed --

Col. 1, line 8; "filled" should read -- filed --

Col. 1, line 33; "Björkland" should read -- Björklund --
Col. 2, line 2; "procedure" should read -- procedures --
Col. 2, line 52; "selectively" should read -- selectivity --
Col. 2, line 61; "has" should read -- had --
Col. 3, line 28; "H$_2$at" should read -- H$_2$O at --
Col. 3, line 41; "abut" should read -- about --
Col. 4, line 10; "propertites" should read -- properties --
Col. 4, line 36; "rotein" should read -- protein --
Col. 4, line 51; "linked gels," should read -- linked dextran gels, --
Col. 5, line 9; "fubber" should read -- buffer --
Col. 5, line 37; "single chain" should read -- single peptide chain --
Col. 5, line 55; "filter used" should read -- filter media used --
Col. 6, line 46; "off" should read -- of --
Col. 7, line 15; "rostate," should read -- prostate, --
Col. 7, line 21; "immunologicall" should read -- immunological --
Col. 7, line 45; "+20°C" should read -- -2°C --
Col. 7, line 50; "+2°C" should read -- -2°C --
Col. 7, line 53; "ethly" should read -- ethyl --
Col. 8, line 26; "preferably and," should read -- preferably 98-100°C and, --

UNITED STATES PATENT AND TRADEMARK OFFICE
CERTIFICATE OF CORRECTION

PATENT NO. : 4,160,018
DATED : July 3, 1979
INVENTOR(S) : Knut Bertil Bjorklund

It is certified that error appears in the above-identified patent and that said Letters Patent are hereby corrected as shown below:

Col. 13, line 20; "medial" should read -- medical --
Col. 13, line 32; "existance" should read -- existence --
Col. 13, line 37; "MCR" should read -- MRC --
Col. 16, line 65; "at homogenized 1000" should read -- at 1000 --
Col. 21, line 23; "concentratin" should read -- concentration --
Col. 24, line 5, first occurrence; "fluoroescent" should read -- fluorescent --

Col. 24, line 22; "havng" should read -- having --

Col. 24, line 36; "and if, not" should read -- and, if not --

Col. 24, line 49; "cells, latex" should read -- cells, latex, --

Signed and Sealed this

Thirtieth Day of October 1979

[SEAL]

Attest:

RUTH C. MASON
Attesting Officer

LUTRELLE F. PARKER
Acting Commissioner of Patents and Trademarks